United States Patent [19]
Zeece, Sr.

[11] Patent Number: 5,868,139
[45] Date of Patent: Feb. 9, 1999

[54] DEVICE FOR A SWIMMER TO CONVENIENTLY REMOVE WATER FROM HIS OR HER EAR

[76] Inventor: Steve Zeece, Sr., 1881 Rice St., St. Paul, Minn. 55113

[21] Appl. No.: 976,144

[22] Filed: Nov. 21, 1997

[51] Int. Cl.[6] .................................................... A61F 11/00
[52] U.S. Cl. ........................................... 128/864; 128/865
[58] Field of Search ........................... 128/846, 864–868; 2/2.14, 2, 428

[56] References Cited

U.S. PATENT DOCUMENTS

| | | | |
|---|---|---|---|
| 2,824,558 | 2/1958 | Michael | 128/865 |
| 3,783,864 | 1/1974 | Moller | 128/864 |
| 4,896,679 | 1/1990 | St. Pierre | 128/864 |
| 5,483,975 | 1/1996 | Hirschenbain | 128/864 |

*Primary Examiner*—Michael A. Brown
*Attorney, Agent, or Firm*—Jacobson and Johnson

[57] ABSTRACT

A hollow earpiece has a bulbous section for insertion into the ear canal and a flange section joined to the bulbous section by a neck with an opening in the tip of the bulbous section to allow water from the ear canal to enter into the bulbous section and an elongated hollow tube coupled to the earpiece at the earpiece neck with one open end of the tube located within the bulbous section and the other open end adaptable for applying a suction to remove water from the user's ear.

4 Claims, 2 Drawing Sheets

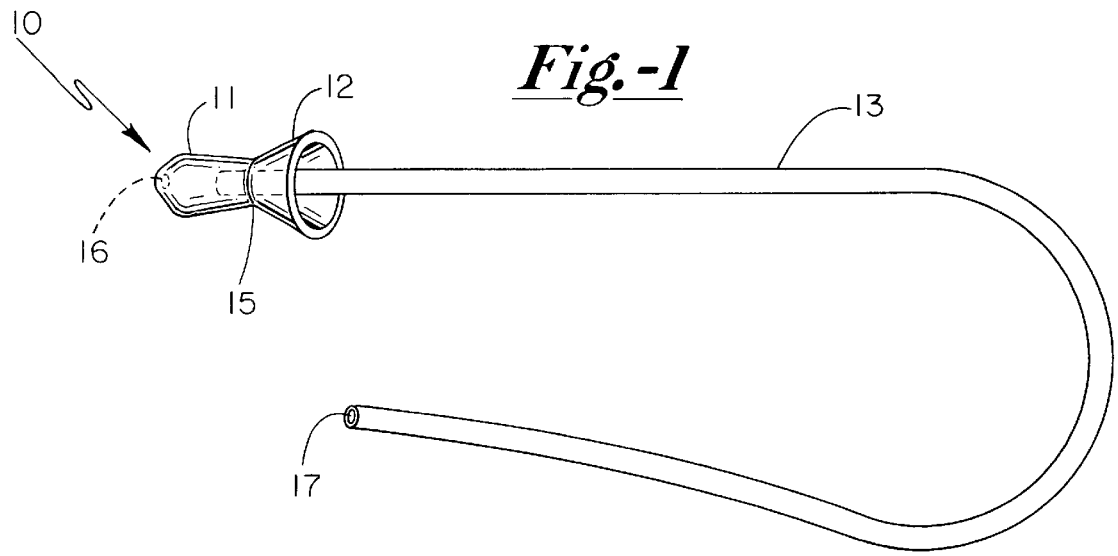
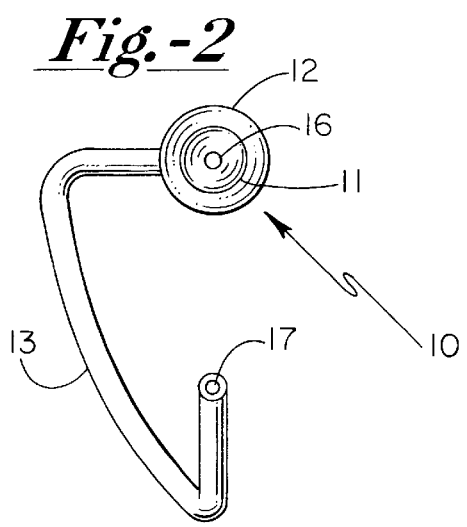
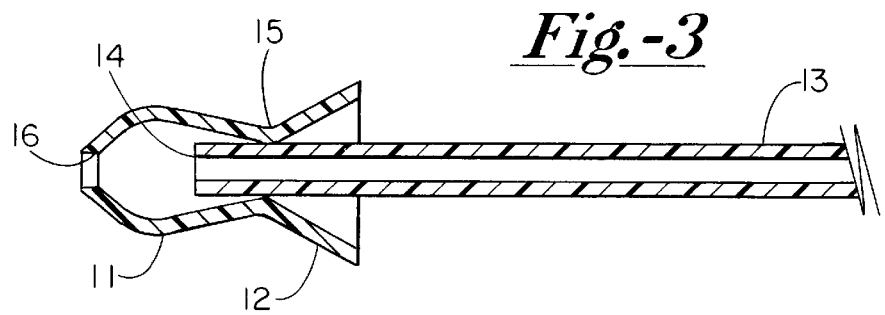

DEVICE FOR A SWIMMER TO CONVENIENTLY REMOVE WATER FROM HIS OR HER EAR

FIELD OF THE INVENTION

This invention is directed toward providing a simple device which a swimmer can use to quickly and easily remove water from his or her ear immediately after swimming.

DESCRIPTION OF THE PRIOR ART

U.S. Pat. No. 5,599,330 by Rainin is a surgical device which uses a wicking principle for removing excess fluid from a person's eye during eye surgery. Another U.S. Pat. No. 4,950,280 by Brennan is a tampon for insertion into the cavity of hemorraging nose for removing the blood and other mucous or fluids in the nasal cavity. Both of these devices utilize a porous absorbing member around the open end of a tube through which suction is applied to aspirate the fluid. In other words, the tube or drainage conduit is not in direct liquid or fluid communication with the interior of the cavity. In both devices the aim is to not apply a suction directly to the affected area but only allow the fluids in the area being drained to seep into the absorption member and then use the drainage conduit to remove these fluids from the absorption member so it can absorb more fluids. The Brennan device also shows a tube having an open end extending through the absorption material into the cavity for the purpose of allowing air to flow into and out of the nasal cavity.

There are other similar devices which utilize a sponge or brush-like materials at the end of a hollow shaft for insertion into a cavity and for withdrawing fluids by suction.

SUMMARY OF THE INVENTION

A earplug or earpiece has a hollow bulbous section for entering partway into the ear canal and a flange section joining the bulbous section at a neck area. A hollow tube is coupled to the earpiece through the neck area with one open end in the interior of the bulbous section and the tube extends away from the ear. The other open end of the tube is adaptable for applying a suction through the tube into the interior of the earpiece. There is an opening at the tip of the bulbous section of the earpiece and preferably the open end of the tube is in direct alignment and direct fluid communication with the opening. Preferably the tube or drainage conduit extends far enough so that the other open end of the tube can be inserted into the users mouth so that he or she can apply a suction to draw water immediately and directly out of the ear canal.

BRIEF DESCRIPTION OF THE DRAWINGS

FIG. 1 is a perspective view of a preferred form of the invention;

FIG. 2 is an end view of the earpiece;

FIG. 3 is a section view; and

DESCRIPTION OF THE PREFERRED EMBODIMENTS

Figure 4:
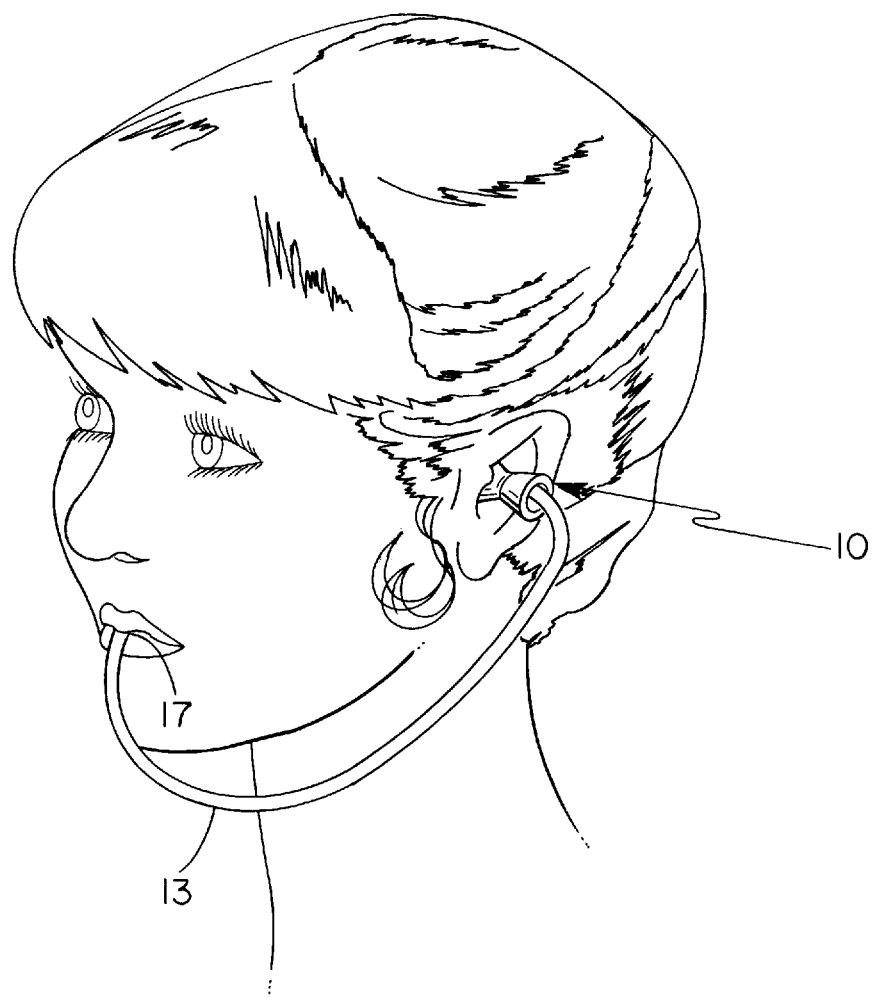
FIG. 4 is an illustration of the preferred form of the invention in use.

Oftentimes a swimmer will have water which will collect in the external ear canal and can be bothersome. In some cases if the water isn't removed quickly, it could cause or facilitate ear infections, fungus growth and other ear ailments. Oftentimes the swimmer will use a plug in the ears to keep the water out of the ear but some of these are quite ineffective. Also, of course it interferes with the swimmer's ability to hear. It is not uncommon for a swimmer to start shaking or striking his or her head in order to try to displace water that might have gotten into the ear canal while swimming. The present invention is aimed at providing a simple, handy, safe device which can be quickly and easily used by the swimmer upon exiting the water to immediately remove virtually all of the water that might have gathered or settled in the ear canal.

A hollow earplug or earpiece, generally designated by reference numeral 10, is preferably made out of a soft fairly resilient rubber or like material and has a bulb-like or bulbous section 11 and an integrally formed flange section 12 joined together at a neck 15. The earpiece material should be soft and somewhat resilient so that it does not damage the ear canal when inserted. A hollow elongated tube 13 coupled to earpiece 10 at neck 15 has one open end 14 located in the interior of the bulbous section 11 and extends away from earpiece 10 beyond flange section 12. Preferably neck 15 fits snugly around tube 13 which helps to hold tube 13 in place and close off the interior of bulbous section 11. An aperture 16 at the tip of the bulbous section 11 provides an opening from the interior of the ear to the interior of the earpiece bulbous section.

As illustrated in FIG. 4, typically earpiece 10 is inserted by the user, a swimmer or bather, into the ear so that the bulbous section 11 enters partway into the ear canal. Tube 13 is preferably made long enough so it reaches the swimmer's mouth and the swimmer can then apply a suction to the other end 17 of tube 13 thereby drawing any water that is in the ear canal directly through opening 16 into the interior of the bulbous section 11. The water is then carried by tube 13 out of the interior of the bulbous section. Generally the amount of water is quite minimal so that there is no problem with the user swallowing any water that has been sucked out of the ear canal. Most of the water from the ear canal goes directly through the opening 16 into the open end of 14 of tube 13 which is in direct alignment and direct fluid communication with opening 16 so that the water in the canal is quickly and easily removed to eliminate or minimize its effect and avoid potential ear damage or infection.

In general the device is small, compact and flexible so that it can be rolled or folded up and easily kept in the pocket of a bathing suit. If the bathing suit does not have a pocket, it can be located convenient to the swimmer (or bather) when he or she exits from the water so that he or she can quickly and easily use the device and put it back in place.

If desired, the earpiece can be slipped off the end of tube 13 and discarded or placed on a new tube.

I claim:

1. A device for conveniently and quickly removing water from a user's ear, comprising:

a) an earpiece having a hollow bulbous section for insertion into the ear canal and a flange section, the junction of said flange section and said bulbous section forming a neck having an opening;

b) said earpiece having an opening at about the tip of said bulbous section for allowing water to enter directly into the interior of said bulbous section from the ear canal;

c) an elongated hollow tube coupled to the earpiece through said neck opening, said tube having one open end located in the interior of said earpiece bulbous section and the other open end adapted for applying suction to said tube to draw fluid from the earpiece and d) said neck snugly surrounding said tube to close off said neck opening and to hold said tube in place.

2. The water removing device as described in claim 1 wherein the one open end of said tube is in line with and located away from the opening in said earpiece bulbous section for fluid communication with said opening.

3. The water removing device as described in claim 1 wherein said tube extends from said earpiece in a user's ear to the users mouth for applying a suction to the other end of said tube.

4. A method for removing water from a swimmer's ear, comprising the steps of:

a) placing one open end of a hollow elongated tube into the interior of a hollow bulbous section of an earpiece which has an aperture at the tip of the bulbous section; then b) placing the bulbous section of the earpiece part way into the ear canal with the aperture in line with the ear canal; and then c) applying suction at the other open end of said tube with the mouth.

\* \* \* \* \*